United States Patent [19]

Picard et al.

[11] Patent Number: 4,957,971

[45] Date of Patent: Sep. 18, 1990

[54] TRANS-6-(2-(N-HETEROARYL-3,5-DISUB-STITUTED)PYRAZOL-4-YL)-ETHYL)-OR ETHENYL)TETRAHYDRO-4-HYDROXYPY-RAN-2-ONE INHIBITORS OF CHOLESTEROL BIOSYNTHESIS

[75] Inventors: Joseph A. Picard; Bruce D. Roth, both of Ann Arbor; Drago R. Sliskovic, Ypsilanti, all of Mich.

[73] Assignee: Warner-Lambert Company, Morris Plains, N.J.

[21] Appl. No.: 280,756

[22] Filed: Dec. 6, 1988

Related U.S. Application Data

[63] Continuation-in-part of Ser. No. 48,473, May 18, 1987, Pat. No. 4,808,621, which is a continuation-in-part of Ser. No. 882,327, Jul. 7, 1986, abandoned.

[51] Int. Cl.$^5$ .............. C07D 403/04; C07D 405/06; A61K 31/495; A61K 31/505

[52] U.S. Cl. ................................. 514/252; 514/256; 514/275; 544/322; 544/328; 544/331; 544/405

[58] Field of Search ............ 544/336, 332, 322, 326, 544/331, 328, 405; 514/252, 256, 275

[56] References Cited

U.S. PATENT DOCUMENTS

| | | | |
|---|---|---|---|
| 3,983,140 | 9/1976 | Endo et al. | 549/417 |
| 4,137,322 | 1/1979 | Endo et al. | 514/548 |
| 4,198,425 | 4/1980 | Mistui et al. | 514/460 |
| 4,255,444 | 3/1981 | Oka et al. | 549/417 |
| 4,262,013 | 4/1981 | Mistui et al. | 514/460 |
| 4,375,475 | 3/1983 | Willard et al. | 514/460 |
| 4,613,610 | 9/1986 | Wareing | 514/406 |
| 4,751,229 | 6/1988 | Heifetz et al. | 514/406 |

OTHER PUBLICATIONS

*New Engl. J. Med.,* Brown et al., 305, No. 9, 515–517 (1981).
*Jama,* 251, No. 3, 351–374 (1984).
*Proc. Soc. Exper. Biol. Med.,* 102:270 (1959).
*Arch. of Biochem. and Biophys.,* 146, 422–427 (1971).
*J. Chem. Soc. Perkin I,* 1165 (1976).

*Primary Examiner*—Alan L. Rotman
*Attorney, Agent, or Firm*—Ruth H. Newston

[57] ABSTRACT

Certain trans-6-[2-(N-heteroaryl-3,5-disubstituted) pyrazol-4-yl)ethyl]- or ethenyl]tetrahydro-4-hydroxy-2H-pyran-2-ones and the corresponding ring-opened acids, esters and N-oxides derived therefrom which are potent inhibitors of the enzyme 3-hydroxy-3-methyl-glutaryl-coenzyme A reductase (HMG CoA reductase) and are thus useful hypolipidemic or hypocholesterolemic agents. Pharmaceutical compositions containing such compounds, and a method of inhibiting the biosynthesis of cholesterol employing such pharmaceutical compositions are also disclosed.

7 Claims, No Drawings

TRANS-6-(2-(N-HETEROARYL-3,5-DISUB-STITUTED)PYRAZOL-4-YL)-ETHYL)-OR ETHENYL)TETRAHYDRO-4-HYDROXYPYRAN-2-ONE INHIBITORS OF CHOLESTEROL BIOSYNTHESIS

CROSS-REFERENCE TO RELATED APPLICATIONS

This application is a continuation-in-part of application Ser. No. 048,473 filed May 18, 1987, now U.S. Pat. No. 4,808,621, issued Feb. 28, 1989, which is a continuation-in-part of application Ser. No. 882,327 filed July 7, 1986, abandoned.

BACKGROUND OF THE INVENTION

The present invention is related to compounds and pharmaceutical compositions useful as hypocholesterolemic and hypolipidemic agents. More particularly, this invention concerns certain trans-6-[2-(N-heteroaryl-3,5-disubstituted)pyrazol-4-yl)ethyl]- or ethenyl]tetrahydro-4-hydroxy-2H-pyran-2-ones and the corresponding ring-opened acids derived therefrom which are potent inhibitors of the enzyme 3-hydroxy-3-methylglutaryl-coenzyme A reductase (HMG CoA reductase), pharmaceutical compositions containing such compounds, and a method of inhibiting the biosynthesis of cholesterol employing such pharmaceutical compositions.

High levels of blood cholesterol and blood lipids are conditions involved in the onset of arteriosclerosis. It is well known that inhibitors of HMG-CoA reductase are effective in lowering the level of blood plasma cholesterol, especially low density lipoprotein cholesterol (LDL-C), in man (cf. M. S. Brown and J. L. Goldstein, *New England Journal of Medicine*, 305, No. 9, 515–517 (1981). It has now been established that lowering LDL-C levels affords protection from coronary heart disease (cf. *Journal of the American Medical Association*, 251, No. 3, 351–374 (1984).

Moreover, it is known that certain derivatives of mevalonic acid (3,5-dihydroxy-3-methylpentanoic acid) and the corresponding ring-closed lactone form, mevalonolactone, inhibit the biosynthesis of cholesterol (cf. F. M. Singer et al., *Proc. Soc. Exper. Biol. Med.*, 102: 270 (1959) and F. H. Hulcher, *Arch. Biochem. Biophys.*, 146: 422 (1971)).

U.S. Pat. Nos. 3,983,140; 4,049,495 and 4,137,322 disclose the fermentative production of a natural product, now called compactin, having an inhibitory effect on cholesterol biosynthesis. Compactin has been shown to have a complex structure which includes a mevalonolactone moiety (Brown et al., *J. Chem. Soc. Perkin I* (1976) 1165.

U.S. Pat. No. 4,255,444 to Oka et al. discloses several synthetic derivatives of mevalonolactone having antilipidemic activity.

U.S. Pat. Nos. 4,198,425 and 4,262,013 to Mitsue et al. disclose aralkyl derivatives of mevalonolactone which are useful in the treatment of hyperlipidemia.

U.S. Pat. No. 4,375,475 to Willard et al. discloses certain substituted 4-hydroxytetrahydropyran-2-ones which, in the 4(R)-trans-stereoisomeric form, are inhibitors of cholesterol biosynthesis.

U.S. Pat. No. 4,613,610 discloses certain pyrazole analogs and derivatives of mevalonolactone having utility as hypolipoproteinemic and antiatherosclerotic agents.

SUMMARY OF THE INVENTION

In accordance with the present invention, there are provided certain trans-6-[2-N-heteroaryl-3,5-substituted- pyrazol-1-yl)ethyl]- or ethenyl]tetrahydro-4-hydroxy-2H- pyran-2-ones and the corresponding ring-opened hydroxy-acids derived therefrom which are potent inhibitors of cholesterol biosynthesis by virtue of their ability to inhibit the enzyme 3-hydroxy-3-methylglutaryl coenzyme A reductase (HMG-CoA reductase).

In particular, in its broadest aspect the present invention provides compounds of structural Formula I

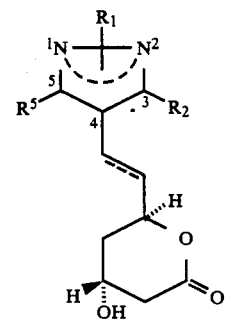

wherein $R_1$ is 2-, 4-, or 5-pyrimidinyl; 2-pyrazinyl; 2-, 3-, or 4-pyridinyl; 2-, 3-, or 4-quinolinyl; 3-phthalazinyl; 9-acridinyl, 3-, 4-, or 5-pyrazolyl; 2-, 4-, or 5-imidazolyl; 2-benzimidazolyl, 2-benzothiazolyl; 2-, or 3-indolyl, 2-, or 3-furanyl; or 2-, or 3-thienyl, or 2-, or 3-pyrrolyl.

$R_2$ is alkyl of from one to three carbon atoms, trifluoromethyl, dialkylamino in which alkyl is one to four carbon atoms, pyrrolidino, piperidino, morpholino or piperazino.

$R_5$ is a saturated carbocyclic ring of from four to seven carbon atoms optionally substituted with alkyl of from one to three carbon atoms; 2-norbornyl; 2-norbornenyl; bicyclo[2.2.2]octyl; or

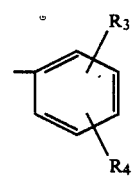

where $R_3$ and $R_4$ are independently hydrogen, alkyl of from one to three carbon atoms, chlorine, or fluorine.

The dotted line in the bridging group connecting the substituted pyrazole group to the pyran-2-one ring is meant to indicate that the bridging group may be either an ethyl (i.e. $-CH_2CH_2-$) or ethenyl (i.e. $-CH=CH-$) group.

The dotted lines in the pyrazole nucleus in Formula I above are meant to indicate that the substituent $R_1$ may be attached to the nitrogen atom at position 1, with double bonds between the atoms at positions 2-3 and 4-5 or, alternatively, $R_1$ may be attached to the nitrogen atom at position 2 with double bonds between the atoms at positions 1-5 and 3-4. (All position numbers corresponding to those in structural Formula I above.)

Also contemplated as falling within the scope of the present invention are the hydroxy acids or esters, pharmaceutically acceptable salts thereof, corresponding to the opening of the lactone ring of the compounds of structural Formula I above, N-oxides, sulphoxides or sulphones thereof.

In another aspect, the present invention provides pharmaceutical compositions useful as hypolipidemic or hypocholesterolemic agents comprising a hypolipidemic or hypocholesterolemic effective amount of a compound in accordance with this invention as set forth above, in combination with a pharmaceutically acceptable carrier.

In yet another aspect, the present invention provides a method of inhibiting cholesterol biosynthesis in a patient in need of such treatment by administering an effective amount of a pharmaceutical composition as defined above.

DETAILED DESCRIPTION

The compounds of the present invention comprise a class of trans-6-[2-N-heteroaryl-3,5-substituted-pyrazol-1-yl)ethyl]- or ethenyl]tetrahydro-4-hydroxy-2H-pyran-2-ones and the corresponding ring-opened hydroxy-acids derived therefrom in which the substituted pyrazole nucleus is attached, through an ethylene or ethenylene group to the remainder of the molecule. When the bridging group between the substituted pyrazole ring and the remainder of the molecule is ethyl, the configuration in the lactone ring is R*R*. Preferred compounds of the present invention are those in which the bridging group between the substituted pyrazole ring and the remainder of the molecule is ethenyl, i.e. —CH=CH—, most preferably in the (E)-trans form and the configuration in the lactone ring is R*S*.

In the compounds of the present invention, position 3 of the pyrazole nucleus (as numbered in structural Formula I above) is substituted with alkyl of from one to three carbon atoms, trifluoromethyl, dialkylamino in which alkyl is one to four carbon atoms, pyrrolidino, piperidino, morpholino or piperazino. Preferred substituents at this position are lower alkyl or dimethylamino, with 1-methylethyl being most preferred.

Position 5 of the pyrazole nucleus (as numbered in structural Formula I above) is substituted with phenyl which is monosubstituted with alkyl of from one to three carbon atoms, fluorine, chlorine or trifluoromethyl, or phenyl which is disubstituted with two groups independently selected from alkyl of from one to three carbon atoms, fluorine, chlorine, or trifluoromethyl. Preferred compounds of the present invention are those in which position 5 is substituted with 4-fluorophenyl.

The compounds of structural Formula I above possess two asymmetric carbon centers, one at the 4-hydroxy position of the pyran-2-one ring, and the other at the 6-position of the pyran-2-one ring where the alkylpyrazole group is attached. This asymmetry gives rise to four possible isomers, two of which are the R-cis- and S-cis- isomers and the other two of which are the R-trans- and S-trans- isomers. This invention contemplates only the trans- form of the compounds of Formula I above.

Examples of compounds contemplated as falling within the scope of the present invention include, but are not limited to the following:

[4α,6α]-6-[2-[5-(4-Fluorophenyl)-3-(1-methylethyl)-1-(2-pyridinyl)-1H-pyrazol-4-yl]ethyl]tetrahydro-4-hydroxy-2H-pyran-2-one.

[4α,6β(E)]-6-[2-[5-(4-Fluorophenyl)-3-(1-methylethyl)-1-(2-pyridinyl)-1H-pyrazol-4-yl]ethenyl]tetrahydro-4-hydroxy-2H-pyran-2-one.

[4α,6α]-6-[2-[5-(4-Fluorophenyl)-3-(1-methylethyl)-1-(2-quinolinyl)-1H-pyrazol-4-yl]ethyl]tetrahydro-4-hydroxy-2H-pyran-2-one.

[4α,6β(E)]-6-[2-[5-(4-Fluorophenyl)-3-(1-methylethyl)-1-(2-quinolinyl)-1-pyrazol-4-yl]ethenyl]tetrahydro-4-hydroxy-2H-pyran-2-one.

[4α,6β]-6-[2-[5-(4-Fluorophenyl)-3-(1-methylethyl)-1-1,3'-bi-1H-pyrazol-4-yl]ethyl]tetrahydro-4-hydroxy-2H-pyran-2-one.

[4α,6β(E)]-6-[2-[5-(4-Fluorophenyl)-3-(1-methylethyl)-1-1,3'-bi-1-pyrazol-4-yl]ethenyl]tetrahydro-4-hydroxy-2H-pyran-2-one.

[4α,6β])-6-[2-[5-(4-Fluorophenyl)-1-(1H-imidazol-4-yl)-3-(1-methylethyl)-1H-pyrazol-4-yl]ethyl]tetrahydro-4- hydroxy-2H-pyran-2-one.

[4α,6β(E)]-6-[2-[5-(4-Fluorophenyl)-1-(1H-imidazol-4-yl)-3-(1-methylethyl)-1H-pyrazol-4-yl]ethenyl]tetrahydro-4-hydroxy-2H-pyran-2-one.

[4α,6β]-6-[2-[1-(1H-Benzimidazol-2-yl)-5-(4-fluorophenyl)-3-(1-methylethyl)-1H-pyrazol-4-yl]ethyl]tetrahydro-4-hydroxy-2H-pyran-2-one.

[4α,6β(E)]-6-[2-[1-(1H-Benzimidazol-2-yl)-5-(4-fluorophenyl)-3-(1-methylethyl)-1H-pyrazol-4-yl]ethenyl]tetrahydro-4-hydroxy-2H-pyran-2-one.

[4α,6β]-6-[2-[1-(9-Acridinyl)-5-(4-fluorophenyl)-3-(1-methylethyl)-1H-pyrazol-4-yl]ethyl]tetrahydro-4-hydroxy-2H -pyran-2-one.

[4α,6β(E)]-6-[2-[1-(9-Acridinyl)-5-(4-fluorophenyl)-3-(1-methylethyl)-1H-pyrazol-4-yl]ethenyl]tetrahydro-4-hydroxy-2H-pyran-2-one.

[4α,6β]-6-[2-[1-(2-Benzothiazolyl)-5-(4-fluorophenyl)-3-(1-methylethyl)-1H-pyrazol-4-yl]ethyl]tetrahydro-4-hydroxy-2H-pyran-2-one.

[4α,6β(E)]-6-[2-[1-(2-Benzothiazolyl)-5-(4-fluorophenyl)-3-(1-methylethyl)-1H-pyrazol-4-yl]ethenyl]tetrahydro-4-hydroxy-2H-pyran-2-one.

[4α,6β]-6-[2-[5-(4-Fluorophenyl)-3-(1-methylethyl)-1-(2-thienyl)-1H-pyrazol-4-yl]ethyl]tetrahydro-4-hydroxy-2H- pyran-2-one.

[4α,6β(E)]-6-[2-[5-(4-Fluorophenyl)-3-(1-methylethyl) -1-(2-thienyl)-1H-pyrazol-4-yl]ethenyl]tetrahydro-4-hydroxy-2H-pyran-2-one.

[4α,6β]-6-[2-[5-(4-Fluorophenyl)-1-(2-furanyl)-3-(1-methylethyl)-1H-pyrazol-4-yl]ethyl]tetrahydro-4-hydroxy-2H-pyran-2-one.

[4α,6β(E)]-6-[2-[5-(4-Fluorophenyl)-1-(2-furanyl)-3-(1-methylethyl)-1H-pyrazol-4-yl]ethenyl]tetrahydro-4-hydroxy-2H-pyran-2-one.

[4α,6β]-6-[2-[5-(4-Fluorophenyl)-3-(1-methylethyl)-1-(1H-pyrrol-2-yl)-1H-pyrazol-4-yl]ethyl]tetrahydro-4-hydroxy-2H-pyran-2-one.

[4α,6β(E)]-6-[2-[5-(4-Fluorophenyl)-3-(1-methylethyl)-1-(1H-pyrrol-2-yl)-1H-pyrazol-4-yl]ethenyl]tetrahydro-4-hydroxy-2H-pyran-2-one.

-[4α,6β(E)]-6-[2-[5-(4-Fluorophenyl)-3-(1-methylethyl)-1-(2-pyrimidinyl)-1H-pyrazol-4-yl]ethenyl]tetrahydro-4-hydroxy-2H-pyran-2-one.

[4α,6β(E)]-6-[2-[5-[4-Fluorophenyl-3-(1-methylethyl)-1-(2-pyrazinyl)-1H-pyrazol-4-yl]ethenyl]tetrahydro-4-hydroxy-2H-pyran-2-one.

[4α,6β]-6-[2-[5-(4-Fluorophenyl)-3-(1-methylethyl)-1-(2-pyrimidinyl)-1H-pyrazol-4-yl]ethyl]tetrahydro-4-hydroxy-2H-pyran-2-one.

[4α,6β]-6-[2-[5-(4-Fluorophenyl)-3-(1-methylethyl)-1-(2-pyrazinyl)-1H-pyrazol-4-yl]ethyl]tetrahydro-4-hydroxy-2H-pyran-2-one.

One reaction sequence which is used to prepare compounds of the present invention is depicted schematically in the following Reaction Sequence (1).

The known or commercially available heteroaryl hydrazine, IV, is reacted with with the desired 1,3-disubstituted diketone, V, to produce the cyclized N-heteroaryl-substituted pyrazole, VIa or VIb. This addition may occur in either of two ways, leading to a substituted pyrazole addition product in which the heterocyclic ring substituent resides on either of the two nitrogen atoms of the pyrazole ring. The predominant product of this reaction, however, is the regioisomer in which the heterocyclic ring is attached to the nitrogen atom adjacent to the carbon which bears the substituted phenyl group (i.e., VIa).

REACTION SEQUENCE (1)

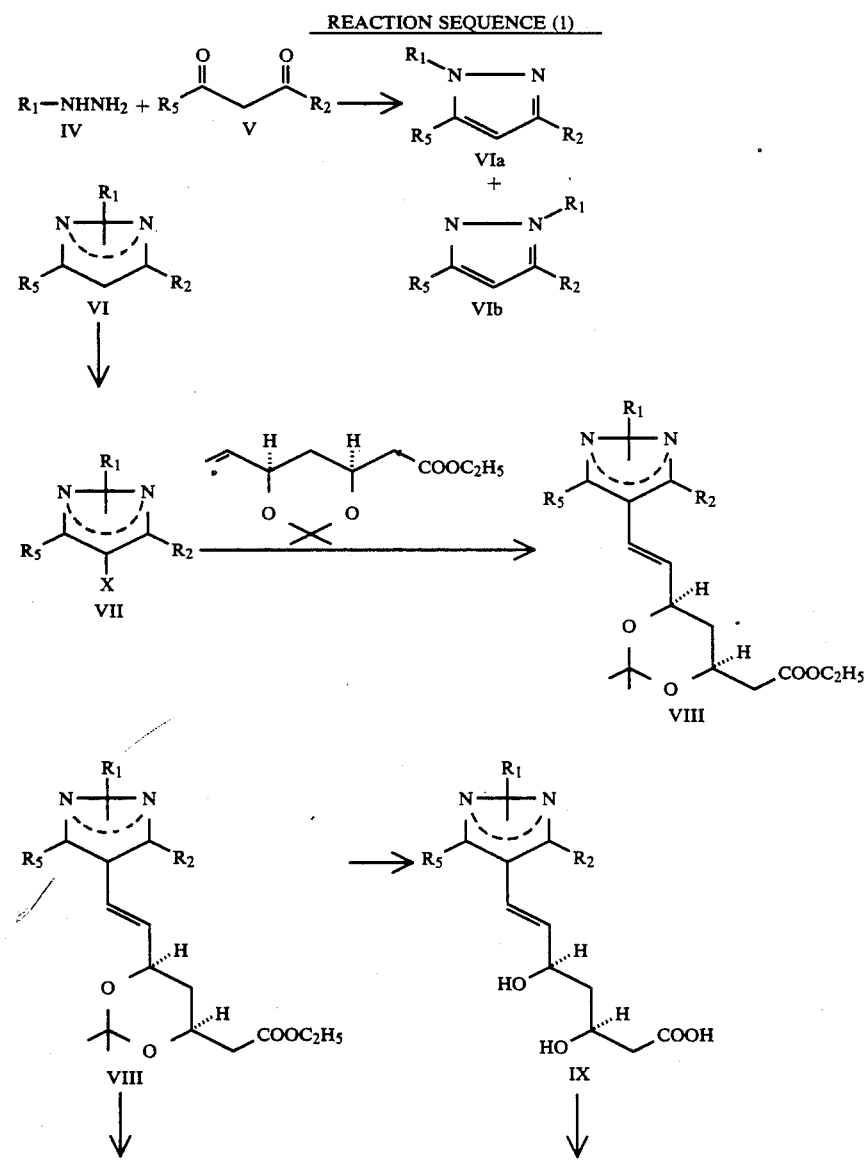

REACTION SEQUENCE (1)
-continued

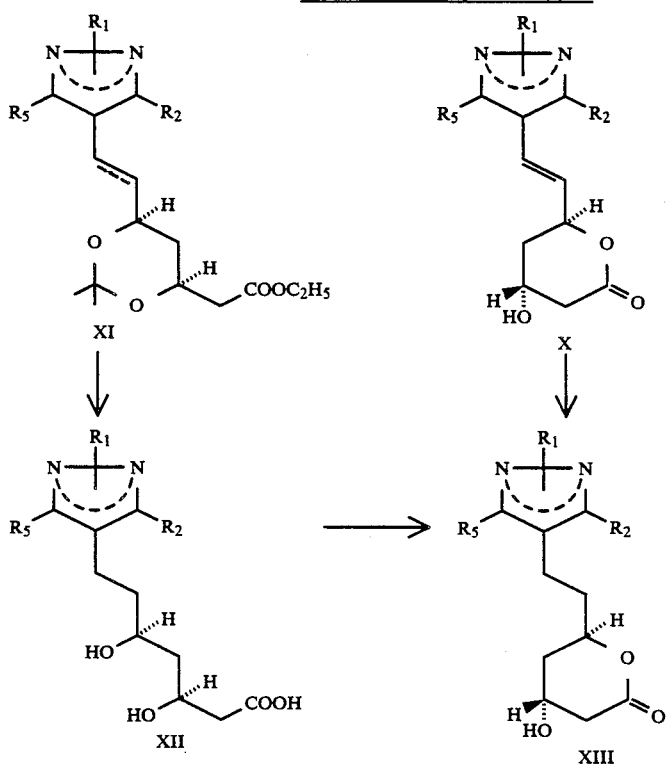

The substituted pyrazole VI is next halogenated by the action of N-bromo- or N-iodosuccinimide in a polar solvent such as dimethylformamide, typically at a temperature below about 10° C. to produce the halogenated derivatives, VII, where X is iodine or bromine.

The 4-halopyrazole compounds, VII, are coupled with 6-ethenyl-2,2-dimethyl-1,3-dioxane-4-acetic acid, methyl or ethyl ester, employing the Heck Reaction (cf. R. F. Heck, *Organic Reactions*, 27: 345–390 (1982) to form VIII.

The pyrazolyl(ethenyl)-1,3-dioxanes, VIII, are saponified and the protecting group removed in the usual manner to produce the corresponding dihydroxyacids, IX, which are employed per se, or as a pharmaceutically acceptable salt, in the pharmaceutical method of this invention. Alternatively, the acids, IX. may be cyclized to the corresponding lactones, X, under mild conditions by a dehydrating agent such as dicyclohexylcarbodiimide.

In a further alternative, the unsaturated dioxanes, VIII, are catalytically reduced under hydrogen to produce the corresponding saturated compounds, XI, which are saponified and deprotected in the usual manner to produce the saturated dihydroxyacids, XII. As with the unsaturated dihydroxyacids, the saturated dihydroxyacids, XII, are employed per se, or as a pharmaceutically acceptable salt in the pharmaceutical method of this invention, or are cyclized to the corresponding saturated lactones, XIII, generally by heating under reflux in toluene with concomitant azeotropic removal of water.

An alternate reaction sequence used to prepare compounds of the present invention beginning with compound VII of Reaction Sequence (1) is depicted schematically in the following Reaction Sequence (2).

REACTION SEQUENCE (2)

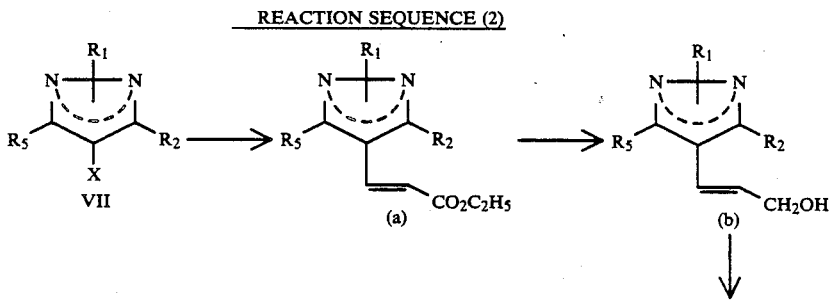

-continued
REACTION SEQUENCE (2)

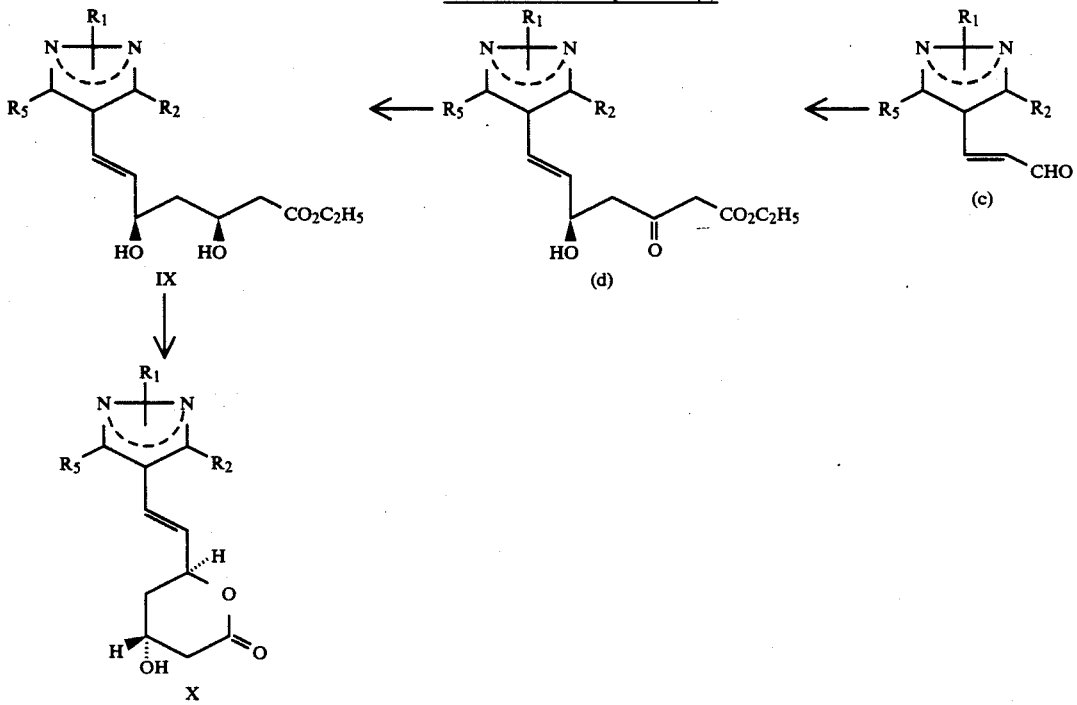

For example, the 4-halopyrazole compounds (VII) are coupled with ethyl acrylate, employing the Heck reaction (cf. R. F. Heck, Org. Reac., 27, 345-390 (1982)). The esters (a) are reduced at −78° C. by the action of diisobutyl aluminum hydride to yield the alcohols (b) which are then oxidized to the corresponding aldehydes (c) with manganese dioxide. Aldol condensation of the aldehydes (c) with the sodium lithium dianion of ethyl acetoacetate at −78° C. in tetrahydrofuran (cf. Kraus et al., J. Org. Chem., 48, 2111 (1983)) gives the 5-hydroxy-β-keto esters (d). The products of this condensation are then reduced in a sequence of steps in which they are first dissolved in a polar solvent such as tetrahydrofuran under dry air atmosphere. A small excess of triethyl borane and catalytic amounts of pivalic acid (2,2-dimethylpropanoic acid) are next added. The mixtures are stirred at room temperature for a short period, then cooled to −78° C.; dry methanol is added followed by sodium borohydride. The mixtures are kept at −78° C. for six hours before treating with ice cold hydrogen peroxide. The substituted 3,5-dihydroxy-6-heptenoic acid ethyl esters (IX) are isolated having the preferred R* S* configuration. The esters (IX) may be hydrolyzed to the sodium salts. The esters (IX) or the free acids produced by acidification of the sodium salts can be dehydrated to the lactones (X) by heating the acid in an inert solvent such as toluene with concomitant azeotropic removal of water.

The ring-opened hydroxy acids or esters of structural formulae IX and XII above are intermediates in the synthesis of the lactone compounds of Formula I and may be used in their free acid form or in the form of a pharmaceutically acceptable metal or amine salt in the pharmaceutical method of the present invention. These acids react to form pharmaceutically acceptable metal and amine salts. The term "pharmaceutically acceptable metal salt" contemplates salts formed with the sodium, potassium, calcium, magnesium, aluminum, iron, and zinc ions. The term "pharmaceutically acceptable amine salt" contemplates salts with ammonia and organic nitrogenous bases strong enough to form salts with carboxylic acids. Bases useful for the formation of pharmaceutically acceptable nontoxic base addition salts of compounds of the present invention form a class whose limits are readily understood by those skilled in the art.

The free acid form of compounds of the present invention may be regenerated from the salt form, if desired, by contacting the salt with a dilute aqueous solution of an acid such as hydrochloric acid.

The base addition salts may differ from the free acid forms of the compounds of this invention in such physical characteristics as solubility and melting point, but are otherwise considered equivalent to the free acid form for the purposes of this invention.

The compounds of the present invention may exist in solvated or unsolvated form. In general, the solvated forms with pharmaceutically acceptable solvents such as water, ethanol and the like, are equivalent to the unsolvated forms for the purposes of this invention.

The compounds of the present invention in lactone or free acid form may be further converted to their corresponding N-oxides by mild oxidation methods known in the art using, for example, peracetic acid, perbenzoic acids or hydrogen peroxide with an appropriate solvent and an optional catalyst.

The compounds of this invention are useful as hypocholesterolemic or hypolipidemic agents by virtue of their ability to inhibit the biosynthesis of cholesterol through inhibition of the enzyme 3-hydroxy-3-methylglutaryl-coenzyme A reductase (HMG-CoA reductase).

The ability of compounds of the present invention to inhibit the biosynthesis of cholesterol was measured by two methods. A first method (designated CSI screen) utilized the procedure described by R. E. Dugan et al., Archiv. Biochem. Biophys., (1972), 152, 21–27. In this method, the level of HMG-CoA enzyme activity in standard laboratory rats is increased by feeding the rats a chow diet containing 5% cholestyramine for four days, after which the rats are sacrificed.

The rat livers are homogenized, and the incorporation of $^{14}C$-acetate into nonsaponifiable lipid by the rat liver homogenate is measured. The micromolar concentration of compound required for 50% inhibition of sterol synthesis over a one-hour period is measured, and expressed as an $IC_{50}$ value.

A second method (designated COR screen) employed the procedure detailed by T. Kita, et al., *J. Clin. Invest.*, (1980), 66: 1094–1100. In this method, the amount of $^{14}C$-HMG-CoA converted to $^{14}C$-mevalonate in the presence of a purified enzyme preparation of HMG-CoA reductase was measured. The micromolar concentration of compound required for 50% inhibition of cholesterol synthesis was measured and recorded as an $IC_{50}$ value.

The activity of representative examples of compounds in accordance with the present invention appears in Table 1, and are compared with that of the prior art compound, compactin.

TABLE 1

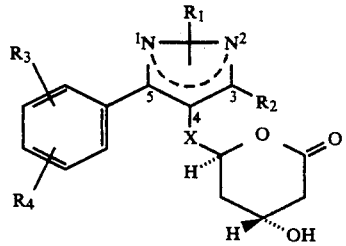

| Compound | X | $R_1$ | $R_2$ | $R_3$ | $R_4$ | $IC_{50}$ (Micromoles/liter) CSI | COR |
|---|---|---|---|---|---|---|---|
| 1 | —CH$_2$CH$_2$— | 1-(2-pryidinyl) | —CH(CH$_3$)$_2$ | H | 4-F | 0.039 | 0.11 |
| 2 | —CH=CH— | 1-(2-pyridinyl) | —CH(CH$_3$)$_2$ | H | 4-F | 0.022 | 0.025 |
| 3 | —CH=CH— | 1-(2-pyrazinyl) | —CH(CH$_3$)$_2$ | H | 4-F | 0.02 | 0.069 |
| 3 | —CH=CH— | 1-(2-pyrimidinyl) | —CH(CH$_3$)$_2$ | H | 4-F | 0.024 | 0.018 |
| 4 | —CH=CH— | 1-(2-benzothiazolyl) | —CH(CH$_3$)$_2$ | H | 4-F | 0.032 | 0.059 |
| Compactin (Prior art) | | | | | | 0.026 | 0.028 |

For preparing pharmaceutical compositions from the compounds of this invention, inert, pharmaceutically acceptable carriers can be either solid or liquid. Solid form preparations include powders, tablets, dispersable granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active compounds is mixed with the carrier having the necessary binding properties in suitable proportions and compacted in the shape and size desired.

For preparing suppositories, a low-melting wax such as a mixture of fatty acid glycerides and cocoa butter is first melted, and the active ingredient is dispersed therein by, for example, stirring. The molten homogeneous mixture is then poured into convenient sized molds and allowed to cool and solidify.

Powders and tablets preferably contain between about 5 to about 70% by weight of the active ingredient. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner, cachets are also included. Tablets, powders, cachets, and capsules can be used as solid dosage forms suitable for oral administration.

Liquid form preparations include solutions suitable for oral or parenteral administration, or suspensions and emulsions suitable for oral administration. Sterile water solutions of the active component or sterile solutions of the active component in solvents comprising water, ethanol, or propylene glycol may be mentioned as examples of liquid preparations suitable for parenteral administration.

Sterile solutions may be prepared by dissolving the active component in the desired solvent system, and then passing the resulting solution through a membrane filter to sterilize it or, alternatively, by dissolving the sterile compound in a previously sterilized solvent under sterile conditions.

Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

In therapeutic use as hypolipidemic or hypocholesterolemic agents, the compounds utilized in the pharmaceutical method of this invention are administered to the patient at dosage levels of from 40 mg to 600 mg per day. For a normal human adult of approximately 70 kg or body weight, this translates to a dosage of from about 0.5 mg/kg to about 8.0 mg/kg of body weight per day.

The dosages, however, may be varied depending upon the requirements of the patient, the severity of the condition being treated, and the compound being employed. Determination of optimum dosages for a particular situation is within the skill of the art.

The following examples illustrate particular methods for preparing compounds in accordance with this invention. These examples are illustrative and are not to be read as limiting the scope of the invention as it is defined by the appended claims.

EXAMPLE 1

Preparation of
[4α,6β]-6-[2-[5-(4-Fluorophenyl)-3-(1-methylethyl)-1-(2-pyridinyl)-1H-pyrazol-4-yl]ethyl]tetrahydro-4-hydroxy-2H-pyran-2-one

Step A—Preparation of 1-(4-fluorophenyl)-4-methyl-1,3-pentanedione

A mixture of 4-fluoroacetophenone (150 g, 1.09 mol) and ethyl isobutyrate (126 g, 1.09 mol) in 1.5 liters of dioxane was added dropwise under a nitrogen atmosphere to a vigorously stirred suspension of hexane-washed sodium hydride (133 g, 3.25 mol, 58.8% NaH) in 3.0 liters of dioxane. Vigorous evolution of gas ensued, after which the mixture was heated to 80°–90° C. for four hours.

The mixture was then allowed to cool to room temperature after which it was poured into six liters of 2 M hydrochloric acid. The resulting mixture was cooled to 0° C. with vigorous stirring and extracted four times with 1-liter portions of chloroform.

The combined chloroform extracts were washed twice with 500 ml portions of water, twice with 500 ml portions of brine solution, and then dried over anhydrous magnesium sulfate. The mixture was filtered to remove undissolved solids, and the filtrate was concentrated under vacuum.

Distillation of the residue yielded 116 g (50%) of 1-(4-fluorophenyl)-4-methyl-1,3-pentanedione, b.p. 100°–110° C. at 1 torr. The infrared spectrum of a thin film of the product showed principal absorption peaks at 2973 and 1603 reciprocal centimeters.

The 100 MHz proton magnetic resonance spectrum of the product in deuterochloroform showed peaks at 1.25 (d, J=7 Hz, 6H), 2.60 (m, J=7 Hz, 1), 6.1 (m, 2H), 6.1 (s, 1H), 7.15 (m, 2H), and 7.9 (m, 2H) parts per million downfield from the tetramethylsilane signal.

Step B—Preparation of 2-[5-(4-Fluorophenyl)-3-(1-methylethyl)-1H-pyrazol-1-yl]pyridine To a solution of 10 g (48 mmol) of 1-(4-fluorophenyl)-4-methyl-1,3-pentanedione in 100 ml of glacial acetic acid was added, under a nitrogen atmosphere at room temperature, 5.77 g (53 mmol) of 2-hydrazinopyridine.

This mixture was then heated at 60° C. for three hours, cooled to room temperature, and poured into 100 ml of water. The resulting mixture was extracted with diethyl ether and the organic layer was separated, washed successively with saturated sodium bicarbonate solution, water, and brine. The ether solution was dried over anhydrous magnesium sulfate, and concentrated under vacuum.

The crude product was flash chromatographed on a silica gel column, eluting with 20% ethyl acetate in hexane to yield 8.7 g of 2-[5-(4-fluorophenyl)-3-(1-methylethyl)-1H-pyrazol-1-yl]pyridine, mp 80°–81° C.

The 200 MHz proton magnetic resonance spectrum of a deuterochloroform solution of the product exhibited peaks at 8.35 (d, 1H); 7.0–7.8 (m, 7H); 6.35 (s, 1H); 3.15 (m, 1H); and 1.3 (d, 6H) parts per million downfield from the tetramethylsilane signal.

Step C—Preparation of 2-[4-bromo-5-(4-Fluorophenyl)-3-(1methylethyl)-1H-pyrazol-1-yl]pyridine N-Bromosuccinimide (7.9 g, 28 mmol) was added to a mixture of 2-[5-(4-fluorophenyl)-3-(1-methylethyl)-1-pyrazol-1-yl]pyridine (7.89 g, 28 mmol) and 30 ml of dimethylformamide at 0° C.

The resulting mixture was stirred at 0° C. for four hours and then poured into 100 ml of water. The white solid which precipitated was collected by filtration and dried to yield 9.0 g of 2-[4-bromo-5-(4-fluorophenyl)-3-(1-methylethyl)-1H-pyrazol-1-yl]pyridine, mp 98°–100° C.

The 200 MHz proton magnetic resonance spectrum of a deuterochloroform solution of the product exhibited peaks at 8.3 (d, 1H); 7.0–7.8 (m, 7H); 3.1–3.2 (m, 1H); and 1.4 (d, 6H) parts per million down field from the tetramethylsilane signal.

Step D—Preparation of cis-(±)-ethyl 6-[2-[5-(4-Fluorophenyl)-3-(1-methylethyl)-1-(2-pyridinyl)-1H-pyrazol-4-yl]ethenyl]-2,2-dimethyl-1,3-dioxane-4-acetate bis-(Tri-O-tolylphosphine) palladium (II) chloride (0.21 g, 2 mmol %) was added to a stirred solution of 6-ethenyl-2,2-dimethyl-1,3-dioxane-4-acetic acid, ethyl ester (5.54 g, 24.3 mmol) in 30 ml of a 50:50 mixture of triethylamine and dimethylformamide.

The mixture was heated to reflux (~120° C.) and 5 g (13.9 mmol) of 2-[4-bromo-5-(4-fluorophenyl)-3-(1-methylethyl)-1H-pyrazol-1-yl]pyridine was added. This mixture was heated under reflux for two hours, at which point a further 0.15 g (1.5 mmol %) of catalyst was added. The mixture was heated under reflux for another twenty-four hours during which an additional 2 mmol % of catalyst was added to the mixture.

The mixture was then cooled to room temperature and poured into 50 ml of water. The mixture which resulted was extracted with diethyl ether, and the ether extract washed successively with portions of water and brine and then dried over anhydrous magnesium sulfate.

The ether solution was concentrated, and the crude product was flash chromatographed on a silica gel column eluting with 20% ethyl acetate in hexane to yield 1.44 g of cis-(±)-ethyl 6-[2-[5-(4-fluorophenyl)-3-(1-methylethyl)-1-(2-pyridinyl)-1H-pyrazol-4-yl]ethenyl]-2,2-dimethyl-1,3-dioxane-4-acetate.

The 200 MHz proton magnetic resonance spectrum of a deuterochloroform solution of the product exhibited peaks at 8.2 (d, 1H); 6.9–7.7 (m, 7H); 6.3 (d, 1H); 5.6 (dd, 1H); 4.3 (m, 2H); 4.0 (q, 2H); 3.2 (s, 1H); 2.56 (dd, 1H); 2.4 (dd, 1H); and 1.3–1.6 (m, 17H) parts per million downfield from the tetramethylsilane signal.

Step E—Preparation of (R*, R*)-7-[5-(4-Fluorophenyl)-3-(1-methylethyl)-1-(2-pyridinyl)-1H-pyrazol-4-yl]-3,5-dihydroxy-6-heptenoic acid A solution of 1.44 g (2.84 mmol) of cis-(±)-ethyl-6-[2[5-(4-fluorophenyl)-3-(1-methylethyl)-1-(2-pyridinyl)-1H- pyrazol-4-yl]ethenyl]-2,2-dimethyl-1,3-dioxane-4-acetate in 15 ml of ethyl acetate was catalytically reduced under one atmosphere of hydrogen gas in the presence of 20% Pd/C. at 25° C. for four days.

The catalyst was removed by filtration and the filtrate was concentrated. The residue was dissolved in 4 ml of 50:50 tetrahydrofuran:1 molar hydrochloric acid and stirred for three hours. The mixture was then made basic by the addition of 25% aqueous sodium hydroxide solution, and the mixture was stirred for thirty minutes.

This mixture was diluted with water, extracted with diethyl ether, and then acidified. The acidified water layer was extracted twice with ethyl acetate and the combined extracts were washed with brine and dried over anhydrous magnesium sulfate. Evaporation of the solvent yielded (R*, R*)-7-[5-(4-fluorophenyl)-3-(1-methylethyl)-1-(2-pyridinyl)-1H-pyrazol-4-yl]-3,5-dihydroxy-6-heptanoic acid.

Step F—Preparation of [4α,6β]-6-[2-[5-(4-Fluorophenyl)-3-(1-methylethyl)-1-(2-pyridinyl)-1H-pyrazol-4-yl]ethyl]-tetrahydro-4-hydroxy-2H-pyran-2-one The crude (R*, R*)-7-[5-(4-fluorophenyl)-3-(1-methylethyl)-1-(2-pyridinyl)-1H-pyrazol-4-yl]-3,5-dihydroxy-6-heptanoic acid from the previous step was lactonized by heating it under reflux in toluene for one hour with azeotropic removal of water. After cooling to room temperature the mixture was concentrated and the residue was flash chromatographed on a silica gel column, eluting with 75% ethyl acetate in hexane to yield pure [4α,6β]-6-[2-[5-(4-fluorophenyl)-3-(1-methylethyl)-1-(2-pyridinyl)-1H-pyrazol-4-yl]-ethyl]-tetrahydro-4-hydroxy-2H-pyran-2-one, mp 182°–184° C. (after recrystallization from 10% ethyl acetate in hexane).

Analyzed for $C_{24}H_{26}FN_3O_2$: Calculated: C, 68.07%; H, 6.19%; N, 9.92%; Found: C, 67.76%; H, 6.18%; N, 9.57%.

The infrared spectrum of a potassium bromide pellet of the product exhibited principal absorption peaks at 2965, 2871, 1719, 1591, 1511, 1478, 1228, 1145, and 1051 reciprocal centimeters.

The 200 MHz proton magnetic resonance spectrum of a deuterochloroform solution of the product exhibited peaks at 8.82 (d, 1H); 7.0–7.9 (m, 7H); 5.2 (d, 1H); 4.5 (m, 1H); 4.1 (m, 1H); 3.1 (h, 1H); 2.3–2.7 (m, 4H); 1.6–1.8 (m, 4H); and 1.3 (d, 6H); parts per million downfield from the tetramethylsilane signal.

EXAMPLE 2

Preparation of [4α,6β(E)]-6-[2-[5-(4-Fluorophenyl)-3-(1-methylethyl)-1-(2-pyridinyl)-1H-pyrazol-4-yl]ethenyl]tetrahydro-4-hydroxy-2H-pyran-2-one Step A—Preparation of trans-3-[5-(4-Fluorophenyl)-3-(1-methylethyl)-1-(2-pyridinyl)-1H-pyrazol-4-yl]-2-propenoic acid, ethyl ester Bis(triphenylphosphine) palladium (II) chloride (11.7 g, 16.6 mmol, 4 mol %) and ethyl acrylate (226 ml, 2.08 mol) were dissolved in DMF (600 ml) and $Et_3N$ (600 ml) and heated to reflux under an inert atmosphere until a homogenous solution resulted. The bromopyrazole (150 g, 0.42 mol, see Step C, Example 1) was then added and the resulting solution heated to reflux overnight, an additional 2 g of the catalyst was also added. The reaction was then cooled and partitioned between ether and water. The organic layer was separated and washed with water and brine, dried over $MgSO_4$, concentrated in-vacuo to yield 191 g of a yellow solid which was recrystallized from 5:1 hexane/ethyl acetate to yield 105 g of white colorless crystals (67%), mp 114°–116° C.

$^1$H NMR ($CDCl_3$) δ 8.28 (dd, 1H), 7.77 (m, 1H), 7.56 (m, 2H), 7.0–7.3 (m, 4H), 6.0 (d, 1H), 4.2 (q, 2H), 3.34 (m, 1H), 1.62 (d, 6H), 1.28 (tr, 3H) ppm.

Step B—Preparation of trans-3-[5-(4-Fluorophenyl)-3-(1-methylethyl)-1-(2-pyridinyl)-1H-pyrazol-4-yl]-2-propen-1-ol To a solution of the unsaturated ester (50 g, 0.132 mol, Step A) in $CH_2Cl_2$ (350 ml) at −78° C. under an inert atmosphere was added di-isobutyl aluminum hydride (290 ml, 0.29 mol, 1 M soln. in $CH_2Cl_2$) dropwise. After stirring for one hour at −78° C., the reaction was quenched by addition of a saturated aqueous solution of sodium sulphate (41 g) and removal of the cooling bath. The reaction mixture was allowed to warm to room temperature and then filtered through celite and sand. The filtrate was dried over $MgSO_4$, filtered and concentrated in-vacuo to yield a white solid which was recrystallized from EtOAc-Hexane (1:1) to give 34.1 g of pure product (77%), mp 106°–109° C.

$^1$H NMR ($CDCl_3$): δ 8.28 (dd, 1H), 7.74 (m, 1H), 7.0–7.3 (m, 6H), 6.4 (d, 1H), 5.9 (dtr, 1H), 4.2 (br.d, 2H), 3.2 (m, 1H), 2.4 (d, 6H) ppm.

Step C—Preparation of trans-3-[5-(4-Fluorophenyl)-3-(1-methylethyl)-1-(2-pyridinyl)-1H-pyrazol-4-yl]-2-propenal Manganese IV dioxide (72.2 g, 0.83 mol) was suspended in toluene and refluxed for four hours with azeotropic removal of water. The unsaturated alcohol (28 g, 0.083 mol, Step B) was added and heating to reflux continued for 24 hours. The suspension was then cooled to room temperature and filtered through a bed of silica. The filtrate was concentrated in-vacuo to give 27.0 g of pure produce (98%), mp 105°–107° C.

$^1$H NMR ($CDCl_3$) δ 9.45 (d, 1H), 8.25 (d, 1H), 2.75 (m, 1H), 7.58 (d, 1H), 7.0–7.3 (m, 6H), 6.36 (dd, 1H), 3.26 (m, 1H), 1.42 (d, 6H) ppm.

Step D—Preparation of trans-7-[5-(4-Fluorophenyl)-3-(1-methylethyl)-1-(2-pyridinyl)-1H-pyrazol-4-yl]-5-hydroxy-3-oxo-6-heptenoic acid, ethyl ester To a hexane washed suspension of NaH (1.8 g, 60% oil dispersion, 45.0 mmol) in THF (50 ml) at 0° C. under an inert atmosphere, was added a solution of ethyl acetoacetate (5.23 ml, 41 mmol) in THF (40 ml). The resulting clear solution was stirred at 0° C. for 20 minutes before n-BuLi (17.1 ml, 41 mmol, 2.4 M soln. in hexane) was added dropwise. The resulting orange solution was stirred at 020 C. for an additional 15 minutes before it was cooled to −78° C. and a solution of the unsaturated aldehyde (12.5 g, 37.3 mmol, Step C) in THF (50 ml) was added dropwise over 20 minutes. The resulting solution was stirred at −78° C. for one hour and then quenched by the addition of glacial acetic acid (20 ml) and removal of the cooling bath. The reaction mixture was then partitioned between EtOAc and water. The organic extracts were washed with water, dried over $MgSO_4$, filtered and concentrated in-vacuo to yield a product which was flash chromatographed on silica gel. Elution with 25% EtOAc-toluene gave 9.0 g of product (52%) and 5.1 g of starting unsaturated aldehyde (Step C) which was resubmitted to the reaction conditions to yield an additional 5.2 g of product.

$^1$H NMR (CDCl$_3$) δ 8.2 (d, 1H), 6.8–7.5 (m, 7H), 6.2 (d, 1H), 5.5 (dd, 1H), 4.4 (m, 1H), 4.0 (q, 2H), 3.3 (s, 2H), 3.1 (m, 1H), 2.5 (d, 2H), 1.3 (d, 6H), 1.1 (tr, 3H) ppm.

Step E—Preparation of (R*, S*, trans)-7-[5-(4-Fluorophenyl)-3-(1-methylethyl)-1-(2-pyridinyl)-1H-pyrazol-4-yl]-3,5-dihydroxy-6-heptenoic acid, ethyl ester Triethylborane (33.8 ml 1 M soln. in THF, 33.8 mmol) was added via a syringe to a soution of the β-keto ester (14.3 g, 30.7 mmol, Step D) and pivalic acid (0.31 g, 3.07 mmol) in THF (100 ml) under a dry air atmosphere with stirring. This was stirred at room temperature for five minutes before cooling to −78° C. Methanol (12 ml) was added followed by sodium borohydride (1.28 g, 33.8 mmol). The resulting solution was stirred at −78° C. for six hours. The reaction was quenched by slow addition to an ice cold solution of 30% hydrogen peroxide (60 ml). This was allowed to warm to room temperature overnight. The reaction mixture was then partitioned between CHCl$_3$ and water. The organic extracts were washed exhaustively with water and dried over $MgSO_4$, filtered and concentrated in-vacuo to yield 16.8 g of crude product which was used in the next step without further purification.

Step F—Preparation of [4α,6β(E)]-6-[2-[5-(4-Fluorophenyl)-3-(1-methylethyl)-1-(2-pyridinyl)-1H-pyrazol-4-yl]ethenyl]-tetrahydro-4-hydroxy-2H-pyran-2-one The dihydroxy ester (16.8 g, 35.9 mmol, Step E) was dissolved in THF (150 ml) and MeOH (100 ml) and 1 N NaOH (36 ml, 35.9 mmol) was added. The resulting solution was stirred at room temperature for one hour, and then concentrated in-vacuo. The residue was re-dissolved in water and washed with diethyl ether. The aqueous solution was then acidified with 1 N HCL and then extracted with ethyl acetate. The organic extract was washed extensively with water, dried over $MgSO_4$, filtered and concentrated in-vacuo to yield crude dihydroxy acid. This was then re-dissolved in toluene (200 ml) and heated to reflux with azeotropic removal of water for three hours. This was then cooled to room temperature and concentrated in-vacuo. The residue was flash chromatographed, elution with 25% EtOAc-toluene gave 10 g of product which was recrystallized from toluene to give 6.33 g of pure white product, mp 131°–133° C.

$^1$H NMR (CDCl$_3$) δ 8.25 (d, 1H), 7.74 (m, 1H), 7.4 (m, 1H), 7.0–7.2 (m, 5H), 6.4 (d, 1H), 5.6 (dd, 1H), 5.15 (m, 1H), 4.3 (m, 1H), 3.22 (m, 1H), 2.7 (m, 2H), 1.7–2.0 (m, 3H), 1.38 (d, 6H) ppm.

EXAMPLE 3

Preparation of [4α,6β(E)]-6-[2-[5-(4-Fluorophenyl-3-(1-methylethyl)-1-(2-pyrazinyl)-1H-pyrazol-4-yl]ethenyl]tetrahydro-4-hydroxy-2H-pyran-2-one

Step A—Preparation of 2-[5-(4-Fluorophenyl)-3-(1-methylethyl)-1H)-pyrazol-1-yl]pyrazine The hydrazino pyrazine (20.20 g, 183 mmol, prepared as in *J. Org. Chem.*, 27, 3243 (1962)) was added in portions to the 1,3-diketone (34.7 g, 167 mmol, prepared in Example 1, Step A) in glacial acetic acid (400 ml). The reaction was refluxed for two hours, concentrated, and partitioned between EtOAc and K$_2$CO$_3$ (aq). The organics were dried (MgSO$_4$) and evaporated to give a brown solid. Recrystallization from hexanes afforded 29.27 g (62%) of a cream colored solid.

$^1$H NMR Spectrum (CDCl$_3$) δ 8.84 (s, 1H), 8.34 (d, 1H), 8.17 (m, 1H), 7.30–6.83 (m, 4H), 6.29 (s, 1H), 3.20–2.89 (m, 1H), 1.35 (d, 6H) ppm.

Step B—Preparation of 2-[4-bromo-5-(4-Fluorophenyl)-3-(1-methylethyl-1H-pyrazol-1-yl]pyrazine N-Bromosuccinimide (18.45 g, 104 mmol) was added in one portion to a solution of the above pyrazole (29.2 g, 104 mmol) in DMF (500 ml) at 0° C. under an inert atmosphere. This was allowed to warm to room temperature overnight. The reaction was poured into 500 ml ice water. The precipitate was collected and dried on a vacuum filter to give 33.00 g (88%) of product as a white solid.

$^1$H NMR (CDCl$_3$): δ 8.85 (s, 1H), 8.32 (d, 1H), 8.06 (m, 1H), 7.32–6.57 (m, 4H), 3.27–2.95 (m, 1H), 1.38 (d, 6H) ppm.

Step C—Preparation of trans-3-[5-(4-Fluorophenyl)-3-(1-methylethyl)-1-(2-pyrazinyl)-1H-pyrazol-4-yl]-2-propenoic acid, ethyl ester Bis(triphenylphosphine) palladium (II) chloride (2.55 g, 3.6 mmol) and ethyl acrylate (49.2 ml, 454 mmol) were dissolved in DMF (200 ml) and Et$_3$N (200 ml) at reflux under an inert atmosphere. The bromopyrazole (32.82 g, 91 mmol), Step B) was then added and the reaction was refluxed overnight. An additional 0.005 eq of catalyst and 10 ml of ethyl acrylate were added to push the reaction to completion. The reaction was cooled and partitioned between H$_2$O and EtOAc. The organic layer was dried (MgSO$_4$) and evaporated to give a brown oil. Elution from a 6-inch silica column gave 20.3 g (59%) of a tan solid. Recrystallization from hexanes produced a brilliant white solid.

$^1$H NMR (CDCl$_3$): δ 8.91 (s, 1H), 8.32 (d, 1H), 8.05 (m, 1H), 7.42 (d, 1H0, 7.26–6.90 (m, 4H), 5.92 (d, 1H), 4.13–3.97 (q, 2H), 3.40–3.07 (m, 1H), 1.42 (d, 6H), 1.25 (tr, 3H) ppm.

Step D—Preparation of trans-3-[5-(4-Fluorophenyl)-3-(1-methylethyl)-1-(2-pyrazinyl)-1H-pyrazol-4-yl]2-propen-1-ol Di-isobutyl aluminum hydride (29 ml, 29 mmol) was added dropwise to a solution of the unsaturated ester (5.0 g, 13.1 mmol, Step C) in CH$_2$Cl$_2$ (150 ml) at −78° C. under an inert atmosphere. After one hour, reaction was incomplete and so an additional 1.1 eq of DIBAL was added. After an additional hour at −78° C, the reaction was quenched by adding 25 ml saturated aqueous Na$_2$SO$_4$, and removing the cooling bath. The reaction was filtered through celite and the filtrate was dried (MgSO$_4$) and evaporated to give an orange oil. Elution from a 3-inch silica column (30% EtOAc/hexanes) gave 2.33 g (52%) of the pyrazinyl-pyrazole product as a yellow solid.

$^1$H NMR (CDCl$_3$): δ 8.82 (s, 1H), 8.23 (d, 1H), 8.06–7.97 (m, 1H), 7.28–6.85 (m, 4H), 6.29 (d, H), 5.79 (dt, 1H), 4.07 (bd, 2H), 3.34–3.03 (m, 1H), 1.98 (bs, 1H), 1.40 (d, 6H) ppm.

Also obtained 0.90 g (26%) of 1H-pyrazole product as a white solid, mp 119°–123° C.

$^1$H NMR (CDCl$_3$): δ 7.57 (q, 2H), 7.08 (t, 2H), 6.47 (d, 1H), 5.90 (dt, 1H), 4.22 (d, 2H), 3.39 (bs, 2H), 3.33–3.19 (m, 1H), 1.36 (d, 6H) ppm.

Step E—Preparation of trans-3-[5-(4-Fluorophenyl)-3-(1-methylethyl)-1-(2-pyrazinyl)-1H-pyrazol-4-yl]-2-propenal Manganese IV dioxide (13.3 g, 153 mmol) was suspended in toluene (300 ml) and refluxed overnight with the azeotropic removal of H$_2$O. The unsaturated alcohol (5.17 g, 15.3 mmol, Step D) was added and reflux was continued for four hours. The reaction was cooled and filtered through a bed of silica. Filtrate was evaporated to give 4.73 g (92%) of product as a yellow solid.

$^1$H NMR (CDCl$_3$): δ 9.32 (d, 1H), 8.90 (s, 1H), 8.29 (d, 1H), 8.03 (m, 1H), 7.27–6.90 (m, 5H), 6.18 (dd, 1H), 3.35–3.04 (m, 1H), 1.41 (d, 6H) ppm.

Step F—Preparation of trans-7-[5-(4-Fluorophenyl)-3-(1-methylethyl)-1-(2-pyrazinyl)-1H-pyrazol-4-yl]-5-hydroxy-3-oxo-6-heptenoic acid, ethyl ester To a hexane washed suspension of NaH (0.90 g, 22.5 mmol) in THF (30 ml) at 0° C. under an inert atmosphere, was added a solution of ethyl acetoacetate (2.69 ml, 21.1 mmol) in THF (30 ml). The resulting clear solution was stirred at 0° C. for 15 minutes before n-BuLi (9.6 ml, 21.1 mmol) was added dropwise. The orange solution was stirred at 0° C. for 15 minutes before it was cooled to −78° C. and a solution of the unsaturated aldehyde (4.73 g, 14.1 mmol, Step E) in THF (80 ml) was added dropwise. This was stirred at −78° C. for two hours and then it was quenched by adding ~5 ml HOAc and removing the cooling bath. The reaction was partitioned between Et$_2$O and 5% K$_2$CO$_3$ (aq). The organics were dried (MgSO$_4$) and evaporated to give a yellow oil. Elution from a 4-inch silica column gave 3.17 g (48%) of product as a yellow foam.

$^1$H NMR (CDCl$_3$) δ 8.87 (s, 1H), 8.27 (d, 1H), 8.04 (m, 1H), 7.27–6.87 (m, 4H), 6.31 (d, 1H), 5.62 (dd, 1H), 4.67–4.42 (m, 1H), 4.25–4.01 (q, 2H), 3.40 (s, 2H), 3.31–3.00 (m, 1H), 2.69 (d, 2H), 1.40 (d, 6H), 1.25 (tr, 3H) ppm.

Step G—Preparation of (R*, S*, trans)-7-[5-(4-Fluorophenyl)-3-(1-methylethyl)-1-(2-pyrazinyl)-1H-pyrazol-4-yl]-3,5-dihydroxy-6-heptenoic acid, ethyl ester Triethyl borane (7.5 ml, 7.5 mmol) was added via syringe to a solution of the β-keto ester (3.17 g, 6.8 mmol, Step F) and pivalic acid (0.069 g, 0.68 mmol) in THF (50 ml) under a dry air atmosphere. The resulting orange solution was cooled to −78° C. and MeOH (10 ml) was added, followed by NaBH$_4$ (0.28 g, 7.5 mmol). The resulting effervescent solution was stirred at −78° C. for five hours. The reaction was quenched by slowly pouring into ice cold H$_2$O$_2$ (5 ml, 30%) and allowing to stir overnight. The reaction was partitioned between H$_2$O and CHCl$_3$. The organics were washed extensively with H$_2$O, dried (MgSO$_4$) and evaporated to give 2.65 g (84%) of a yellow foam which was used in the next step without purification.

Step H—Preparation of (R*,S*,trans)-7-[5-(4-Fluorophenyl)-3-(1-methylethyl)-1-(2-pyrazinyl)-1H-pyrazol-4-yl]-3,5-dihydroxy-6-heptenoic acid The dihydroxy ester (2.65 g, 5.7 mmol, Step G) was dissolved in THF (50 ml) and 1 N NaOH (5.7 ml, 1.0 eq) was added along with MeOH (5 ml) to mix the two phases. The resulting yellow solution was stirred for three hours at room temperature and then it was concentrated to give the sodium salt of the acid. This was partitioned between H$_2$O and Et$_2$O. The aqueous layer was then acidified with 1 N HCl and extracted with EtOAc. The organic layer was dried (MgSO$_4$) and evaporated to give 1.86 g (75%) of a tan foam.

Step I—Preparation of [4α,6β(E)]-6-[2-[5-(4-Fluorophenyl-3-(1-methylethyl)-1-(2-pyrazinyl)-1H-pyrazol-4-yl]ethenyl]-tetrahydro-4-hydroxy-2-H-pyran-2-one The dihydroxy acid (1.86 g, 4.2 mmol) was dissolved in toluene (600 ml) and heated to reflux with the azeotropic removal of H$_2$O, for nine hours. The reaction was then stirred at 90° C. overnight. The reaction was cooled and concentrated to give an orange oil. Elution from a 4-inch silica column gave 0.45 g (47%) of product as an off-white solid.

$^1$H NMR (CDCl$_3$): 8.92 (s, 1H), 8.37 (d, 1H), 8.13 (m, 1H), 7.27–7.05 (m, 4H), 6.40 (d, 1H), 5.70 (dd, 1H), 5.18 (m, 1H), 4.38–4.27 (m, 1H), 3.28–3.17 (m, 1H), 2.78–2.49 (m, 5H), 1.41 (d, 6H) ppm.

EXAMPLE 4

Preparation of [4α,6β(E)]-6-[2-[5-(4-Fluorophenyl)-3-(1)-methylethyl)-1-(2-pyrimidinyl)-1H-pyrazol-4-yl]ethenyl]tetrahydro-4-hydroxy-2H-pyran-2-one

Step A—Preparation of 2-[5-(4-Fluorophenyl)-3-(1-methylethyl)-1H-pyrazol-1-yl]pyrimidine To a solution of 1-(4-fluorophenyl)-4-methyl-1,3-pentanedione (preparation disclosed in Example 1, Step A) (155 g, 0.74 mol) in 1 l glacial acetic acid was added, under a N$_2$ atmosphere at room temperature, 90 g (0.82 mol) of 2-hydrazinopyrimidine (prepared according to J. Chesterfield et al., *J. Chem. Soc.*, 3478, 1955). This was heated to 60° C. for one hour, cooled to room temperature and poured into 4 l saturated NaHCO₃ aqueous solution. The resulting mixture was extracted with EtOAc and the organic layer was separated and washed with water and brine. This solution was dried over MgSO₄, filtered and concentrated in vacuo. The crude reaction mixture was flash chromatographed on a silica gel column, eluting with 10% EtOAc-toluene yielding 16.4 g of 2-[5-(4-fluorophenyl)-3-(1-methylethyl)-1H-pyrazol-1-yl]pyrimidine and 94 g of 5(3)-4-fluorophenyl)-3(5)-(1-methylethyl)-1H-pyrazole, mp 102°-103° C.

90 MHz (CDCl₃) NMR data for both compounds was as follows:

Compound (1): $\delta$ 8.5 (d, 2H), 6.8-7.3 (m, 5H), 6.2 (s, 1H), 3.1 (m, 1H), and 1.3 (d, 6H) ppm Compound (2): $\delta$ 7.5 (m, 2H), 6.7-7.1 (m, 2H), 6.1 (s, 1H), 2.8 (m, 1H), and 1.1 (d, 6H) ppm.

Step B—Preparation of 2-[4-bromo-5-(4-Fluorophenyl)-3-(1-methylethyl)-1H-pyrazol-1-yl]pyrimidine N-Bromosuccinimide (9.97 g, 0.056 mol) was added to a solution of 2-[5-(4-fluorophenyl)-3-(1-methylethyl)-1H-pyrazol-1-yl]pyrimidine (15.8 g, 0.056 mol) in DMF at 0° C. The resulting mixture was allowed to warm to room temperature over 24 hours. This was then poured into 500 ml water. The white solid which precipitated was collected by filtration and dried to yield 16.7 g of 2-[4-bromo-5-(4-fluorophenyl)-3-(1-methylethyl)-1H-pyrazol-1-yl]pyrimidine (3), mp 130°-133° C.

90 MHz ¹H NMR (CDCl ): $\delta$ 8.4 (d, 2H), 6.9-7.3 (m, 5H), 3.2 (m, 1H), 1.4 (d, 6H) ppm.

Step C—Preparation of trans-3-[5-(4-Fluorophenyl)-3-(1-methylethyl)-1-(2-pyrimidinyl)-1H-pyrazole-2-propenoic acid, ethyl ester Ethyl acrylate (16.2 ml, 0.15 mol) and bis-(triphenylphosphine) palladium (II) chloride (0.84 g, 0.0012 mol) in DMF (75 ml) and Et₃N (75 ml) was heated together at reflux under N₂ with stirring until a homogeneous solution resulted. 2-[4-Bromo-5-(4-fluorophenyl))-3-(1-methylethyl)-1H-pyrazol-1-yl]pyrimidine (3) (10.8 g, 0.03 mol) was added and the resulting solution was heated at reflux for 24 hours, during which, an additional 1 mol % of catalyst was added. The mixture was then cooled to room temperature and diluted with ether and water. The organic layer was separated and washed with water and brine, dried over MgSO₄, filtered and concentrated in vacuo. The resulting solid (10.4 g) was recrystallized from hexane/ethyl acetate, mp 155°-162° C.

¹H NMR (CDCl₃): $\delta$ 8.5 ppm (d, 2H), $\delta$ 7.3 (d, 1H, J=24 Hz), 6.9-7.2 (m, 5H), 5.8 (d, 1H, J=24 Hz), 41 (q, 2H), 3.3 (m, 1H), 1.4 (d, 6H), 1.2 (tr, 3H) ppm.

Step D—Preparation of trans-5-(4-Fluorophenyl)-3-(1-methylethyl)-1-(2-pyrimidinyl)-1H-pyrazole-2-propenal To a solution of trans-5-(4-fluorophenyl)-3-(1-methylethyl)-1-(2-pyrimidinyl)-1H-pyrazole-2-propenoic acid, ethyl ester (10 g, 0.026 mol) in 100 ml of dry CH₂Cl₂ at −78° C. was added dropwise 2.5 equivalents of a solution of di-isobutyl aluminum hydride (1 M in CH₂Cl₂) under a N₂ atmosphere. After addition, the resulting solution was stirred at −78° C. for two hours, the cooling bath was removed and the reaction quenched by the addition of 10 g (2.5 eq) of a saturated aqueous solution of sodium sulphate. The resulting mixture was filtered through diatomaceous earth and sand. The solids were washed with hot EtOAc and the combined filtrates were dried over MgSO₄, filtered and concentrated in vacuo. Flash chromatography of the crude reaction mixture eluting with 25% EtOAc-toluene gave 2.0 g of a product identified as starting material. Also eluted was 1.6 g of a product tentatively assigned the dihydropyrimidine structure.

¹H NMR (CDCl₃) evidence was as follows: $\delta$ 6.8 (m, 5H), 5.5-6.1 (m, 4H), 4.0 (d, 2H), 3.7 (br.s, 1H), 3.1 (m, 1H), 1.2 (d, 6H) ppm.

This crude product (1.6 g) was dissolved in toluene and added to a refluxing toluene suspension of MnO₂ (23.4 g, 0.27 mol). This was heated at reflux overnight with azeotropic removal of water using a Deans Stark apparatus. This was then cooled to room temperature and the suspension was then filtered through celite and silica gel. The filtrate was concentrated in-vacuo and the resulting solid recrystallized from EtOAc-hexane, mp 115°-125° C.

¹H NMR (CDCl₃) $\delta$ 9.4 (d, 1H), 8.4 (d, 2H), 7.0-7.3 (m, 6H), 6.1-6.4 (d of d, 1H), 3.3 (m, 1H), 1.4 (d, 6H) ppm.

Step E—Preparation of trans-7-(4-Fluorophenyl-3-(1-methylethyl)-1-(2-pyrimidinyl)-1H-pyrazol-4-yl]-5-hydroxy-3-oxo-6-heptenoic acid, ethyl ester To a stirred suspension of 0.3 g (0.0074 mol, 60% NaH) of hexane washed NaH in 25 ml THF cooled to 0° C. under N₂ was added a solution of ethyl acetoacetate (0.88 ml, 0.0069 mol) in THF (10 ml). When gas evolution was complete, 2.8 ml (0.0069 mol) of a 2.5 M hexane solution of n-butyl lithium was added dropwise. The resulting solution was stirred an additional 30 minutes at 0° C. and then cooled to −78° C. A solution of 1.55 g (0.046 mol) of the compound of Step D in 15 ml THF was added dropwise. The resulting solution was stirred at −78° C. for a further two hours when the reaction was quenched by addition of 10 ml glacial acetic acid. The mixture was partitioned between water and EtOAc. The organic layer was separated, washed with water and brine and dried over MgSO₄, filtered and evaporated to yield a yellow oil which was flash chromatographed on silica gel eluting with 40% EtOAc-toluene giving 0.5 g of starting material and 0.6 g of the desired compound which was used in the next step without any further purification.

¹H NMR (CDCl₃) $\delta$ 8.5 ppm (d, 2H), 6.9-7.3 (m, 5H), 6.3 (d, 1H), 5.5 (d of d, 1H), 4.2 (m, 1H), 4.1 (q, 2H), 3.2 (s, 2H), 3.1 (m, 1H), 2.6 (d, 2H), 1.4 (d, 6H), 1.2 (tr, 3H) ppm.

Step F—Preparation of [4α,6β(E)]-6-[2-[5-(4-Fluorophenyl)-3-(1-methylethyl)-1-(2-pyrimidinyl)-1H-pyrazol-4-yl]ethenyl]-tetrahydro-4-hydroxy-2H-pyran-2-one Triethylborane (1.42 ml, 1 M solution, 0.00142 mol) was added in a single portion to a solution of the compound of Step E (0.6 g, 0.00129 mol) and 13.2 mg of pivalic acid (0.00013 mol) in THF (40 ml) under a dry air atmosphere. This solution was stirred for five minutes before 10 ml of air was bubbled through the solution. The mixture was then cooled to −78° C. and 5 ml MeOH and 53.6 mg of NaBH₄ were added. The mixture was stirred at −78° C. for six hours and then poured into 15 ml of 30% aqueous H₂O₂. This was stirred at room temperature overnight and then diluted with water and extracted with CHCl$_3$. The organic layer was separated, washed with water and brine, dried over MgSO$_4$, filtered and evaporated to yield 0.6 g of the dihydroxy ester which was used without further purification.

The above compound (0.6 g) was dissolved in methanol (20 ml) and 1.28 ml 1 N NaOH was added. This solution was stirred at room temperature for three hours. The solution was then concentrated and the resulting residue re-dissolved in water. This aqueous layer was acidified with 1 N HCl and then extracted with EtOAc. The organic layer was washed with water and brine and dried over MgSO$_4$, filtered and evaporated to yield 0.4 g crude product. This was re-dissolved in toluene (75 ml) and the resulting mixture was heated under reflux for four hours with azeotropic removal of water. The reaction mixture was then concentrated and the residue flash chromatographed on silica gel eluting with 50% EtOAc-toluene, to yield 0.17 g of the title compound, mp 164°–166° C.

$^1$H NMR (CDCl$_3$) δ 8.6 (d, 2H), 7.0–7.2 (m, 5H), 6.3–6.4 (d, 1H), 5.6–5.7 (d of d, 1H), 5.2 (m, 1H), 4.3 (m, 1H), 3.2 (m, 1H), 2.5–2.7 (m, 2H), 1.7–1.9 (m, 2H), 1.4 (d, 6H) ppm.

EXAMPLE 5

Preparation of
[4α,6β(E)]-6-[2-[1-(2-Benzothiazolyl)-5-(4-fluorophenyl)-3-(1-methylethyl)-1H-pyrazol-4-yl]ethenyl]tetrahydro-4-hydroxy-2H-pyran-2-one

Step A—Preparation of 2-[5-(4-Fluorophenyl)-3-(1-methylethyl)-1H-pyrazol-1-yl]benzothiazole To a solution of the 1,3-diketone (103 g, 495 mmol) (preparation described in Example 1, Step A) in glacial acetic acid (800 ml) was added 2-hydrazinobenzothiazole (85.8 g, 520 mmol). The resulting solution was refluxed for 2.5 hours and then cooled to room temperature overnight. The resulting precipitate was collected, washed with water and dried overnight to give 154 g (92%) of a cream colored solid.

$^1$H NMR Spectrum (CDCl$_3$): δ 7.80 (dd, 1H), 7.68 (dd, 1H), 7.58–7.50 (m, 2H), 7.42–7.27 (m, 2H), 7.16–7.07 (m, 2H), 6.35 (s, 1H), 3.17–3.03 (m, 1H), 1.35 (d, 6H) ppm.

Step B—Preparation of 2-[4-Bromo-5-(4-fluorophenyl)-3-(1-methylethyl)-1H-pyrazol-1-yl]benzothiazole N-Bromosuccinimide (86.5 g, 486 mmol) was added in portions to the pyrazole (164 g, 486 mmol, Step A) in DMF (1l) at 0° C. under an atmosphere of N$_2$. This mixture was stirred and allowed to warm to room temperature overnight. The reaction mixture was poured into H$_2$O (1 l) and the resulting precipitate was collected and washed with water. The product was dried overnight to give 184.1 g (91%), mp 146°–147° C. (hexanes).

$^1$H NMR Spectrum (CDCl$_3$) δ 7.79 (dd, 1H), 7.64 (d, 1H), 7.55–7.48 (m, 2H), 7.40–7.28 (m, 2H), 7.22–7.15 (m, 2H), 3.23–3.14 (m, 1H), 1.44 (d, 6H) ppm.

Step C—Preparation of trans-3-[1-(2-Benzothiazolyl)-5-(4-fluorophenyl-3-(1-methylethyl)-1H-pyrazol-4-yl]-2-propenoic acid, ethyl ester Ethyl acrylate (39 ml, 360 mmol) and the palladium catalyst (2.02 g, 2.9 mmol) (previously described) were mixed in DMF (100 ml) and Et$_3$N (100 ml) and heated to reflux to give a homogeneous solution. The bromopyrazole (30 g, 72 mmol, Step B) was added and the reaction was refluxed for 24 hours under an inert atmosphere. The reaction was cooled, and partitioned between H$_2$O and Et$_2$O. The combined organic extracts were dried (MgSO$_4$) and evaporated to give a brown oily solid. Recrystallization from hexanes gave 23.60 g (75%) of product as a cream colored solid.

$^1$H NMR Spectrum (CDCl$_3$) δ 7.75 (dd, 1H), 7.60 (dd, 1H), 7.53–7.16 (m, 7H), 6.00 (d, 1H), 4.19 (q, 2H), 3.33–3.23 (m, 1H), 1.44 (d, 6H), 1.31–1.25 (tr, 3H) ppm.

Step D—Preparation of trans-3-[1-(2-Benzothiazolyl)-5-(4-fluorophenyl)-3-(1-methylethyl)-1H-pyrazol-4-yl]-2-propen-1-ol To a suspension of the unsaturated ester (23.60 g, 54 mmol, Step C) in CH$_2$Cl$_2$ (400 ml) at −78° C. under an inert atmosphere, was added, dropwise, a solution of di-isobutyl aluminum hydride in methylene chloride (119 ml, 119 mmol). The reaction was stirred for 1.5 hours and TLC. indicated incomplete reaction. An additional aliquot of di-isobutyl aluminum hydride (60 ml, 60 mmol) was added dropwise and the reaction was stirred for an additional 2.5 hours at −78° C. The reaction was quenched by adding 100 ml saturated Na$_2$SO$_4$ solution and removing the cooling bath. The reaction was stirred at room temperature overnight and filtered through diatomaceous earth. The filtrate was dried (MgSO$_4$) and evaporated to give 13.82 g (65%) of a tan solid which was used in the next step without further purification.

$^1$H NMR Spectrum (CDCl$_3$): δ 7.72 (d, 1H), δ7.60 (d, 1H), 7.56–7.12 (m, 6H), 6.30 (d, 1H), 5.95–5.85 (dtr, 1H), 4.17 (d, 2H), 3.28–3.17 (m, 1H), 1.98 (br.s., 1H), 1.42 (d, 6H) ppm.

Step E—Preparation of trans-3-[1-(2-Benzothiazolyl)-5-(4-fluorophenyl)-3-(1-methylethyl)-1H-pyrazol-4-yl]-2-propenal Manganese dioxide (30.0 g, 350 mmol) was suspended in toluene (600 ml) and refluxed overnight under an inert atmosphere, with azeotropic removal of H$_2$O. The crude unsaturated alcohol (13.82 g, 35 mmol, Step D) was added and the reaction was heated to reflux for eight hours with the azeotropic removal of H$_2$O. The reaction was cooled to room temperature overnight, concentrated to dryness and the residue was eluted from a 4-inch silica column (CH$_2$Cl$_2$/EtOAc) to give 7.5 g (55%) product as a white solid.

$^1$H NMR Spectrum (CDCl$_3$): δ 9.37 (d, 1H), 7.75–6.97 (m, 9H), 6.23 (dd, 1H), 3.32–3.02 (m, 1H), 1.44 (d, 1H) ppm.

Step F—Preparation of trans-7-[1-(2-Benzothiazolyl)-5-(4-fluorophenyl)-3-(1-methylethyl)-1H-pyrazol-4-yl]-5-hydroxy-3-oxo-6-heptenoic acid, ethyl ester To a hexane washed suspension of NaH (1.23 g, 30.7 mmol) in THF (20 ml) at 0° C. under an inert atmosphere, was added a solution of ethyl acetoacetate (3.66 ml, 28.7 mmol) in THF (20 ml). The resulting clear solution was stirred at 0° C. for 15 minutes before n-BuLi (13.1 ml, 28.7 mmol) was added dropwise. This orange solution was stirred at 0° C. for 15 minutes before it was cooled to −78° C. and a solution of the unsaturated aldehyde (7.50 g, 19.2 mmol, Step E) in THF (100 ml) was added dropwise. The reaction was stirred at −78° C. for one hour and then it was quenched by adding 4 ml glacial acetic acid and removing the cooling bath. The reaction mixture was partitioned between Et$_2$O and saturated aqueous K$_2$CO$_3$ solution. The organic extracts were dried (MgSO$_4$) and evaporated to give an orange solid. Recrystallization from hexanes gave 8.71 g (87%) of product as a pale yellow orange solid.

$^1$H NMR Spectrum (CDCl$_3$): δ 7.70–6.90 (m, 8H), 6.32 (d, 1H), 5.60 (dd, 1H), 4.90–4.48 (m, 1H), 4.27–4.03 (q, 2H), 3.39 (s, 2H), 3.30–2.95 (m, 1H), 2.80 (br.s., 1H), 2.65 (d, 2H), 1.40 (d, 6H), 1.32–1.14 (tr, 3H) ppm.

Step G—Preparation of
(R*,S*,trans)-7-[1-(2-Benzothiazolyl)-5-(4-fluorophenyl)-3-(1-methylethyl)-1H-pyrazol-4-yl]-3,5-dihydroxy-6-heptenoic acid, ethyl ester Triethyl borane (17.3 ml, 17.3 mmol) was added via syringe to a solution of the β-keto ester (8.18 g, 15.7 mmol, Step F) and pivalic acid (0.16 g, 1.6 mmol) in THF (150 ml) under a dry air atmosphere. The resulting orange solution was stirred for 15 minutes at room temperature. The reaction was then cooled to −78° C. and MeOH (20 ml) was added, followed by addition of NaBH$_4$ (0.65 g, 17.3 mmol). The resulting solution was stirred at −78° C. for seven hours before it was quenched by carefully pouring into ice-cold aqueous H$_2$O$_2$ (7 ml, 30%) and stirring overnight. The reaction mixture was partitioned between H$_2$O and CHCl$_3$. The organic layer was dried (MgSO$_4$) and evaporated to give 7.40 g (90%) of a yellow foam which was used in the next step without further purification.

The above dihydroxy ester (7.28 g, 13.9 mmol) was dissolved in 150 ml THF and 10 ml MeOH, and 1 N NaOH (14.6 ml) was added. This was stirred for one hour and then evaporated to dryness to give the sodium salt of the acid (mp 226°–231° C). This was dissolved in water and washed with diethyl ether. The aqueous layer was acidified with 1 N HCl and extracted with EtOAc. The organic layer was dried (MgSO$_4$) and evaporated to give 5.50 g (80%) of a yellow foam.

Step H—Preparation of
[4α,6β(E)]-6-[2-[1-(2-Benzothiazolyl)-5-(4-fluorophenyl)-3-(1-methylethyl)-1H-pyrazol-4-yl]-ethenyl]-tetrahydro-4-hydroxy-2H-pyran-2-one The dihydroxy acid (5.50 g, 11.1 mmol, Step G) was dissolved in toluene (500 ml) and the solution was heated to reflux with the azeotropic removal of H$_2$O for five hours. The reaction was cooled and concentrated to give a yellow solid. Elution from a 4-inch silica column (EtOAc) gave 4.0 g (75%) of product as an off-white solid, mp 168°–170° C.

$^1$H NMR Spectrum (CDCl$_3$): δ 7.74 (dd, 1H), 7.59 (dd, 1H), 7.44–7.12 (m, 6H), 6.38 (d, 1H), 5.70 (dd, 1H), 5.21–5.13 (m, 1H), 4.40–4.34 (m, 1H), 3.26–3.15 (m, 1H), 2.78–2.58 (m, 2H), 2.00–1.78 (m, 2H), 1.73 (br.s., 1H), 1.41 (d, 6H) ppm.

PREPARATION OF STARTING MATERIALS

Preparation of 5-hydroxy-3-oxo-6-heptenoic acid, ethyl ester

Propenal (0.1 mol, as a 2 M solution in tetrahydrofuran) was added dropwise over a period of thirty minutes to a stirred solution of 0.11 mol of the lithio-sodio salt of ethyl acetoacetate in 200 ml of tetrahydrofuran which had been cooled to 0° C. When addition was complete, the solution was stirred for thirty minutes after which the reaction was quenched by the addition of saturated ammonium chloride solution, followed by 2 M hydrochloric acid solution.

The reaction mixture was extracted with diethyl ether and the ether extract was washed successively with water, saturated sodium bicarbonate solution, and then brine. The ether solution was then dried over anhydrous magnesium sulfate, filtered, and evaporated to yield 14 g of 5-hydroxy-3-oxo-6-heptenoic acid, ethyl ester, contaminated with a slight amount of ethyl acetoacetate starting material.

Preparation of β,δ-dihydroxy-6-heptenoic acid, ethyl ester

Employing a syringe, 10 ml of air were bubbled through a solution of 10 mmol of 5-hydroxy-3-oxo-6-heptenoic acid, ethyl ester and 11 mmol of tributylborane dissolved in 10 ml of anhydrous tetrahydrofuran which was under a nitrogen atmosphere. The resulting mixture was stirred overnight, then cooled to −78° C. after which 12 mmol of sodium borohydride were added. The suspension was allowed to warm slowly to 0° C., at which point the reaction was quenched by the addition of 30 mmol of glacial acetic acid. Methanol (30 ml) was added, followed by 3.3 ml of 30% aqueous hydrogen peroxide solution. This mixture was stirred at 0° C. for sixty minutes, and then partitioned between diethyl ether and water.

The organic layer was separated, washed with brine solution, and then dried over anhydrous magnesium sulfate. The ether solution was evaporated to yield crude β,δ-dihydroxy-6-heptenoic acid, ethyl ester which was used in the subsequent step without further purification.

Preparation of
6-ethenyl-2,2-dimethyl-1,3-dioxane-4-acetic acid, ethyl ester

The crude β,δ-dihydroxy-6-heptenoic acid, ethyl ester from the previous step was dissolved in a mixture of 30 ml of dichloromethane and 10 ml of 2,2-dimethoxypropane. Camphorsulfonic acid (0.05 g) was added, and the mixture was stirred overnight. Concentration of the reaction mixture and flash chromatography of the residue yielded 1.1 g of 6-ethenyl-2,2-dimethyl-1,3-dioxane-4-acetic acid, ethyl ester.

The infrared spectrum of a liquid film of the product showed principal absorption peaks at 2994, 1743, 1439, 1382, 1203, and 1170 cm$^{-1}$.

The 90 MHz proton magnetic resonance spectrum of a deuterochloroform solution of the product showed peaks at 1.2–1.5 (m, 10H), 1.60 (m, 1H), 2.48 (m, 2H), 3.75 (m, 1H), 4.05 (1, 2H, J=7Hz), 4.35 (m, 1H), 5.0–6.0 (m, 3H) parts per million downfield from tetramethylsilane.

We claim:
1. A compound of structural formula I

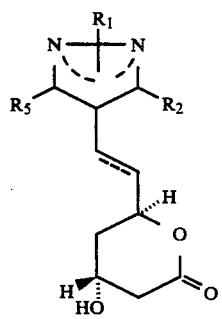

I wherein $R_1$ is 2-, 4-, or 5-pyrimidinyl; or 2-pyrazinyl; and wherein $R_1$ is attached to one of the nitrogen atoms of the pyrazole nucleus;

$R_2$ is alkyl of from one to three carbon atoms or trifluoromethyl;

$R_5$ is a saturated carbocyclic ring of from four to seven carbon atoms optionally substituted with alkyl of from one to three carbon atoms; 2-norbornyl; 2-norbornenyl; bicyclo[2.2.2]octyl; or

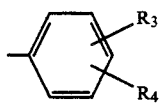

wherein $R_3$ is alkyl of from one to three carbon atoms, chlorine or fluorine, and $R_4$ is hydrogen, alkyl of from one to three carbon atoms, chlorine, or fluorine;

or a ring-opened hydroxy acid or ester derived therefrom, N-oxides thereof or a pharmaceutically acceptable salt thereof.

2. A compound as defined by claim 1 having the formula

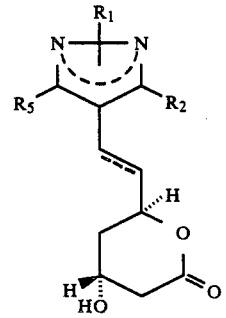

where $R_5$ is

3. A compound as defined in claim 1 having the name [4α,6β]-6-[2-[5-(4-fluorophenyl)-3-(1-methylethyl-1-(2-pyrimidinyl)-1H-pyrazol-4-yl]ethyl]tetrahydro-4-hydroxy-2H-pyran-2-one.

4. A compound as defined in claim 3 having the name [4α,6β(E)]-6-[2-[5-(4-fluorophenyl)-3-(1-methylethyl)-1-(2-pyrimidinyl)-1H-pyrazol-4-yl]ethenyl]tetrahydro-4-hydroxy-2H-pyran-2-one.

5. A compound as defined in claim 3 having the name [4α,6β(E)]4-fluorophenyl)-3-(1-methylethyl)-1-(2-pyrazinyl) -1H-pyrazol-4-yl]ethenyl]tetrahydro-4-hydroxy-2H-pyran-2-one.

6. A pharmaceutical composition, useful as a hypocholesterolemic agent, comprising a hypocholesterolemic effective amount of a compound in accordance with claim 1 in combination with a pharmaceutically acceptable carrier.

7. A method of inhibiting cholesterol biosynthesis in a patient in need of such treatment by administering a pharmaceutical composition as defined by claim 6.

* * * * *